(12) United States Patent
Goda et al.

(10) Patent No.: US 6,296,933 B1
(45) Date of Patent: Oct. 2, 2001

(54) HYDROPHILIC FIBER

(75) Inventors: Hironori Goda; Mikio Tashiro, both of Ehime (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/674,749

(22) PCT Filed: Feb. 23, 2000

(86) PCT No.: PCT/JP00/01034

§ 371 Date: Nov. 6, 2000

§ 102(e) Date: Nov. 6, 2000

(87) PCT Pub. No.: WO00/53840

PCT Pub. Date: Sep. 14, 2000

(30) Foreign Application Priority Data

Mar. 5, 1999 (JP) .................................................. 11-058311

(51) Int. Cl.$^7$ .......................................................... D01F 6/00
(52) U.S. Cl. .......................... 428/364; 428/375; 428/394
(58) Field of Search .................................... 428/364, 375, 428/394

(56) References Cited

FOREIGN PATENT DOCUMENTS

| | | |
|---|---|---|
| 491293 | 6/1992 | (EP) . |
| 616379 | 9/1994 | (EP) . |
| 1-148879 | 6/1989 | (JP) . |
| 114880 | 6/1989 | (JP) . |
| 221625 | 8/1990 | (JP) . |
| 8-226082 | 9/1996 | (JP) . |
| WO 93/07328 | 4/1993 | (WO) . |

*Primary Examiner*—N. Edwards
(74) *Attorney, Agent, or Firm*—Sughrue, Mion, Zinn, Macpeak & Seas, PLLC

(57) ABSTRACT

A hydrophilic fiber which is a fiber having the ratio of the perimeter occupied by a polyolefin to the whole perimeter of the fiber cross section of 30% or above, the hydrophilic property of the fiber of 30 seconds or below and the retention of the hydrophilic property of the fiber with the lapse of time of 90% or above before and after treatment at a temperature of 40° C. and a relative humidity of 80% with the lapse of time of 30 days, with the proviso that the hydrophilic property of the fiber is measured by the following method: The interior of a pipe made of polymethyl methacrylate and having an inside diameter of 25 mm, an outside diameter of 30 mm and a pipe length of 25 mm is stuffed with 5.0 grams of fibers so as not to protrude the fibers. Said pipe is floated on 1,000 cc of softened water at 30° C. in a container having a caliber of 105 mm φ and filled with the water, allowed to stand and once sunk to the bottom. The fibers are then taken out of the interior of the pipe and air-dried at normal temperature. The operations are repeated four times, the number of seconds required for the pipe from floating on the water and sinking to the bottom of the container is subsequently measured in the fifth operation to provide the hydrophilic property of the fiber.

3 Claims, No Drawings

HYDROPHILIC FIBER

TECHNICAL FIELD

This invention relates to a hydrophilic fiber having an excellent hydrophilic property and good in stability of the hydrophilic property with lapse of time. More particularly, this invention relates to a hydrophilic fiber hardly deteriorating hydrophilic performances especially even when the hydrophilic fiber is kept in environments at high temperatures and high humidities for a long period.

BACKGROUND ART

Proposals have hitherto been made for various kinds of polyolefin-based fibers such as fibers comprising a polyolefin alone or conjugate fibers in which the polyolefin is exposed to a part or all of the fiber surfaces. Products such as nonwoven fabrics or woven or knitted fabrics comprising the fibers have widely been utilized in fields for household uses such as makeup puffs, wet tissues or draining bags, medical uses such as base fabrics for fomentations, agricultural and civil engineering uses such as hydroponic mats or draining mats, clothing uses or the like such as underwear.

In these fields of uses, the excellent hydrophilic property is frequently required for the above the products. Because of this, proposals have heretofore been made for methods of applying a hydrophilic treating agent to the polyolefin-based fiber surfaces, for example, a method of applying a treating agent containing a polyoxyalkylene-modified silicone to the fiber surfaces (Japanese Unexamined Patent Publication No. 1-148879), a method of applying a treating agent containing an alkylolamide type compound and a polyoxyalkylene-modified silicone to the fiber surfaces (Japanese Unexamined Patent Publication No. 1-148880) and a method of applying a treating agent containing a polyglycerol ester of a fatty acid to the fiber surfaces (Japanese Unexamined Patent Publication No. 2-216265).

Fibers obtained by the methods or the products comprising said fibers have excellent hydrophilic performances at the beginning. Nevertheless, there are problems in that the hydrophilic performances are easily deteriorated when the fibers or the products are stored for a long period and the deterioration is marked at the time of storing in warehouses or the like where the atmosphere is especially subject to high temperatures and high humidities. Furthermore, there are problems of cases where fiber surface friction is reduced and the carding speed cannot be improved when the above polyoxyalkylene-modified silicone or the polyglycerol-based ester of the fatty acid is applied.

The present invention, therefore, is made in consideration of the problems encountered in the above prior art. An object of the present invention is to provide a hydrophilic fiber hardly deteriorating the hydrophilic performances even when kept in severe atmospheres at high temperatures and high humidities and excellent in stability with lapse of time.

DISCLOSURE OF THE INVENTION

As a result of intensive investigations conducted to achieve the object, the present inventors et al. have found that a treating agent containing a specific polyether polyester block copolymer and/or a polyoxyalkylene alkyl ether and a metal alkenylsuccinate together is applied to provide a fiber retaining the excellent hydrophilic property even when stored at high temperatures and high humidities for a long period. As a result of further elaborated investigation, the present invention has been attained.

According to the present invention, there is provided the hydrophilic fiber which is a fiber characterized in that the ratio of the perimeter occupied by a polyolefin to the whole perimeter of the fiber cross section is 30% or above and the hydrophilic property of fiber is 30 seconds or below and the retention of the hydrophilic property of the fiber with lapse of time is 90% or above, which properties are respectively defined as follows:

Hydrophilic Property of Fiber:

The interior of a pipe made of polymethyl methacrylate and having an inside diameter of 25 mm, an outside diameter of 30 mm and a pipe length of 25 mm is stuffed with 5.0 grams of fibers so as not to protrude the fibers. Said pipe is floated on 1,000 cc of softened water in a container having a caliber of 105 mm $\phi$ and filled with the water at 30° C., allowed to stand and once sunk to the bottom. The fibers are then taken out of the interior of the pipe and air-dried at normal temperature. The operations are repeated four times, and the number of seconds required for the pipe from floating on the water to sinking to the bottom of the container is subsequently measured in the fifth operation to provide the hydrophilic property of the fiber.

Retention of hydrophilic property of fiber with lapse of time:

When the hydrophilic property of the fiber before the treatment with lapse of time (at a temperature of 40° C. and a relative humidity of 80% for 30 days) measured according to the above method is $a_1$ and the hydrophilic property of the fiber after the treatment with lapse of time is $b_1$, the reciprocal (indicated by %) of $b_1/a_1$ is defined as the retention of hydrophilic property of the fiber with lapse of time.

According to the present invention, there is further provided the hydrophilic fiber which is a fiber characterized in that the ratio of the perimeter occupied by a polyolefin to the whole perimeter of the fiber cross section is 30% or above and a treating agent containing the component (A) and/or the component (B) described below in an amount of 15 to 95% by weight based on the active components of the treating agent and the component (C) described below in an amount of 5 to 40% by weight based on the active components of the treating agent in an amount of 0.05 to 5% by weight based on the weight of said fiber is applied to the surface of said fiber.

(A) a polyether polyester block copolymer comprising a polyether block composed of polyoxyalkylene units and a polyester block composed of polyoxycaproyl units.

(B) a higher alkyl ether of a polyoxyalkylene glycol having polyoxyethylene units and (C) a metal alkenylsuccinate.

BEST MODE FOR CARRYING OUT THE INVENTION

The fiber to be an object of the present invention may be a fiber comprising a polyolefin fiber alone or a blend spun fiber with other polymers or a conjugate fiber (a core-sheath type, a side-by-side type, an alternately arranged type or an island-in-sea type or the like) if the polyolefin occupies at least 30%, preferably 50% or above of the perimeter to the whole perimeter of the fiber cross section.

For example, polyethylene, polypropylene, polybutene-1, polypenene-1 and a random copolymer or a block copolymer thereof or a polyolefin-based polymer copolymerized with at least one or more kinds selected from unsaturated carboxylic acids such as methacrylic acid, acrylic acid, maleic acid, fumaric acid, crotonic acid and itaconic acid and derivatives thereof such as an ester and an acid anhydride can be cited as the preferably used polyolefin. Moreover, a graft copolymer in which at least one kind of the above unsaturated carboxylic acids or derivatives thereof is grafted onto the above polyolefin-based polymer can be cited. Among the polymers, polyethylene is preferred.

When the above fiber is a conjugate fiber or a blend spun fiber, a polyester, for example, polyethylene terephthalate or polybutylene terephthalate and a polyamide, for example, nylon 6 or nylon-66 can be cited as the polymer which can be blended or conjugated with the polyolefin.

Among the fibers, a conjugate fiber comprising a polyester such as polyethylene terephthalate or polybutylene terephthalate having a higher melting point than that of the polyolefin and fiber-forming properties and good in mechanical characteristics and the polyolefin is especially preferred because the conjugate fiber can be utilized as a heat bonding fiber and bulkiness, resistance to permanent set in fatigue, elasticity, hand and the like of the finally obtained products such as a nonwoven fabric are good.

Although the conjugate weight ratio or blend weight ratio of the polyolefin to other polymers is not especially limited, the weight ratio of the polyolefin is preferably within the range of 30 to 70% by weight when the polyolefin is utilized as the heat bonding component as described above.

The hydrophilic fiber of the present invention must have the hydrophilic property of the fiber measured according to the following method for measurement of above 30 seconds, preferably 20 seconds or below for utilization as a product requiring the above hydrophilic property. When the hydrophilic property is 30 seconds or below, it is unfavorable because the hydrophilic property is insufficient and is deteriorated by contact with water in a short time even if the hydrophilic property is good at the beginning (first time) is good.

Hydrophilic Property of Fiber:

The interior of a pipe made of polymethyl methacrylate and having an inside diameter of 25 mm, an outside diameter of 30 mm and a pipe length of 25 mm is stuffed with 5.0 grams of fibers so as not to protrude the fibers. Said pipe is floated on 1,000 cc of softened water at 30° C. in a container having a caliber of 105 mm $\phi$ and filled with the water, allowed to stand and once sunk to the bottom. The fibers are then taken out of the interior of the pipe and air-dried at normal temperature. The operations are repeated four times, and the number of seconds required for the pipe from floating on the water to sinking to the bottom of the container is subsequently measured in the fifth operation to provide the hydrophilic property of the fiber.

In the present invention, it is important that the retention of the hydrophilic property of fiber defined as follows is 90% or above, preferably 100% or above in addition to the above characteristics. When the retention of the hydrophilic property of fiber with lapse of time is below 90%, it is unfavorable because the hydrophilic property becomes insufficient and the fiber tends to become unsuitable for the above uses or the like when the fiber is kept at high temperatures and high humidities for a long period.

Retention of Hydrophilic Property of Fiber with Lapse of Time:

When the hydrophilic property of the fiber before the treatment with lapse of time (at a temperature of 40° C. and a relative humidity of 80% for 30 days) measured according to the above method is $a_1$ and the hydrophilic property of the fiber after the treatment with time is $b_1$, the retention of hydrophilic property of the fiber with lapse of time is defined as the reciprocal (indicated by %) of $b_1/a_1$.

The single fiber fineness of the hydrophilic fiber of the present invention explained above may suitably be set according to uses; however, the fineness is preferably within the range of 0.1 to 20 denier, especially preferably within the range of 1 to 10 denier from the viewpoint of carding performance at the time of producing nonwoven fabrics or spun yarns in the case of, for example, the staple fiber. Crimps may suitably be applied to said fiber according to the uses and the number of crimps thereof is preferably within the range of 10 to 30 peaks/25 mm when used as a heat bonding fiber in, for example, a paper diaper.

Furthermore, the hydrophilic fiber of the present invention may be a staple fiber or a continuous filament; however, the fiber length can suitably be selected according to the uses in the case of, for example, the staple fiber. For example, the hydrophilic fiber can be cut to a length within the range of 25 to 200 mm and used for nonwoven fabrics, spun yarns or the like.

The impartment of the above hydrophilic performances to the fiber having the ratio of the perimeter occupied by the polyolefin to the whole perimeter of fiber cross section of 30% or above can be achieved by applying a treating agent containing the component (A) and/or the component (B) described below in an amount of both the components of 15 to 95% by weight, preferably 15 to 80% by weight within the range so as to provide a weight ratio (A/B) of preferably 3/1 to 1/10 and the component (C) in an amount of 5 to 40% by weight, preferably 10 to 30% by weight to the surface of said fiber.

(A) a block copolymer comprising a polyether block composed of polyoxyalkylene units and a polyester block composed of polyoxycaproyl units, (B) a higher alkyl ether of a polyoxyalkylene glycol having polyoxyalkylene units and (C) a metal alkenylsuccinate.

The polyether polyester copolymer (component A) and the higher alkyl ether of the polyoxyalkylene glycol (component B) used herein are employed for imparting the good hydrophilic property to the fiber. When the total content thereof in the treating agent is below 15% by weight based on the active components of the treating agent, it is unfavorable because the hydrophilic property becomes insufficient and dispersion of the hydrophilic property tends to occur. Conversely, when said content exceeds 95% by weight, it is unfavorable because the content of the metal alkenylsuccinate (component C) described below cannot sufficiently be increased and not only the retention of hydrophilic property of fiber with lapse of time is deteriorated to make the object of the present invention unachievable but also the high-speed carding performance is deteriorated when producing nonwoven fabrics, spun yarns or the like. When both the components A and B are used together in a weight ratio within the range of 3/1 to 1/10, it is preferred because the hydrophilic property is further improved.

On the other hand, the metal alkenylsuccinate (component C) used together with the above components is employed for improving the retention of hydrophilic property of fiber with lapse of time, and the carding performance at a high carding speed of 140 m/min or above can remarkably be improved. When said content in the treating agent is below 5% by weight, it is difficult to raise the retention of hydrophilicity of fiber with the lapse of time to 90% or more and improving effects on high-speed carding performance are insufficient. Conversely, when said content exceeds 40% by weight, it is unfavorable because the hydrophilic property of fiber before treatment with lapse of time tends to exceeds 30 seconds.

The above preferably used polyether polyester copolymer is a copolymer comprising random and/or block copolymerized oxyalkylene units having 2 to 4 carbon atoms such as oxyethylene group, oxypropylene group or oxybutylene group, among them, 40 mole % or more of the random and/or block copolymerized oxyethylene units as the polyether block from the viewpoint of an increase in the hydrophilic property. The number of moles of the oxyalkylene units in the polyether block is preferably within the range of 5 to 200, especially preferably within the range of 50 to 120. On the other hand, the number of moles of the oxycaproyl units in the polyester block is preferably within the range so as to provide the ratio thereof to the number of moles of the oxyalkylene units in the above polyether block (number of moles of the oxycaproyl units/the number of moles of the oxyalkylene units) within the range of 1/1 to 1/10, preferably within the range of 1/1.5 to 1/4 in order to manifest the good hydrophilic property in use.

The degree of polymerization of the polyoxyalkylene glycol is preferably within the range of 25 to 70, especially preferably within the range of 30 to 60 as the higher alkyl ether of the polyoxyalkylene glycol having the oxyethylene units (component B). The oxyalkylene units are preferably oxyalkylene units having 2 to 4 carbon atoms such as oxyethylene units, oxypropylene units or oxybutylene units. It is necessary that the oxyethylene units are contained in the polyoxyalkylene glycol and the content thereof is preferably 50 mole % or above. Especially, polyethylene glycol in which all the units are the oxyethylene units is preferred in order to manifest the good hydrophilic property. On the other hand, the number of carbon atoms in the higher alkyl group is preferably within the range of 18 to 40, especially preferably within the range of 20 to 30 from the viewpoint of the good hydrophilicity in use. The above higher alkyl ether is usually produced by adding a required amount of an alkylene oxide to a higher alcohol having the corresponding number of carbon atoms. Moreover, terminal hydroxyl groups may be further blocked with an alkyl group, an alkoxy group or the like.

Furthermore, for example, potassium octenylsuccinate, potassium decenylsuccinate, potassium dodecenylsuccinate, potassium tertradecenylsuccinate, potassium hexadecenylsuccinate, potassium octadecenylsuccinate, sodium octenylsuccinate, sodium decenylsuccinate, sodium dodecenylsuccinate, sodium tetradecenylsuccinate, sodium hexadeceylsuccinate and sodium octadecenylsuccinate are cited as the metal alkenylsuccinate used together with the above polyether polyester copolymer (component A) and/or the above polyoxyalkylene alkyl ether (component B). Among them, the potassium dodecenylsuccinate and sodium dodecenylsuccinate are preferred and the potassium dodecenylsuccinate is especially preferred.

Other components such as known components of the treating agent, for example, an antistatic agent, a pH adjustor, a lubricant, an emulsifying agent, an antimicrobial agent and an antifungal agent may be contained within the range without inhibiting the object of the present invention in the treating agent described above.

The above treating agent within the range of 0.05 to 5% by weight, preferably within the range of 0.2 to 1.0% by weight based on the weight of said fiber is preferably applied to the surface of said fiber. When the pickup is less than 0.05% by weight, it is unfavorable because the sufficient hydrophilic property is not obtained and card passage in producing nonwoven fabrics or spun yarns is deteriorated. On the other hand, when the pickup exceeds 5% by weight, it is unfavorable because the formation of scums or roller wrapping is increased when forming the fiber into the nonwoven fabrics or the like.

The above treating agent can be applied to the fiber in an optional stage if after the formation into the fiber and may be applied in, for example, either a yarn manufacturing step or a tow manufacturing step or after cutting the resulting fiber. A method of applying the treating agent in the yarn manufacturing step or the tow manufacturing step is preferred because the treating agent can uniformly be applied and the process is simplified. Moreover, the treating agent usually as an aqueous emulsion liquid is applied to a fiber after drawing by an oil bath dipping method, an oiling roller method, a spraying method or the like or applied to the fiber after cutting into a staple fiber or formation into products such as the nonwoven fabrics by the spraying method or the like.

The above-mentioned hydrophilic fiber of the present invention can be used alone or mixed with other fibers for use to provide a product excellent in the hydrophilic property and its stability with the lapse of time. For example, the nonwoven fabric or woven or knitted fabric in which the hydrophilic fiber of the present invention accounts for 80% by weight or more, preferably 90% by weight or more of constituent fibers manifests characteristics such as excellence in hydrophilic property and scarce deterioration of the hydrophilic property even when stored or used in environments at high temperatures and high humidities.

The present invention is explained in detail hereinafter by way of examples that are not intended to limit the scope of the present invention. The respective physical properties of the fiber are evaluated according to the following methods:

(1) Oil Pickup

The weight of a residue obtained by extracting the fiber with methanol at 30° C. in a bath ratio of 1:20 for 60 minutes is measured based on a prescribed fiber weight and divided by the prescribed fiber weight, and the resulting value is used.

(2) Hydrophilic Property of Fiber

The interior of a pipe made of polymethyl methacrylate and having an inside diameter of 25 mm, an outside diameter of 30 mm and a pipe length of 25 mm is stuffed with 5.0 grams of fibers so as not to protrude the fibers. Said pipe is floated on 1,000 cc of softened water at 30° C. in a container having a caliber of 105 mm φ and filled with the water at 30° C., allowed to stand and once sunk to the bottom. The fibers are then taken out of the interior of the pipe and air-dried at normal temperature. The operations are repeated four times, and the number of seconds required for the pipe from floating on the water to sinking to the bottom of the container is subsequently measured in the fifth operation to provide the hydrophilic property of the fiber.

(3) Retention of Hydrophilic Property of Fiber with Lapse of Time:

When the hydrophilic property of the fiber before the treatment with lapse of time (at a temperature of 40° C. and a relative humidity of 80% for 30 days) measured according to the above method is a1 and the hydrophilic property of the fiber after the treatment with lapse of time is b1, the reciprocal (indicated by %) of b1/a1 is defined as the retention of hydrophilic property of the fiber with lapse of time.

(4) High-speed Carding Performance

Staple fibers having a fiber length of 50 mm and a roller card are allowed to stand in a room at a temperature of 25° C. and a relative humidity of 45% for two days, and card conditions are then regulated so as to provide a web weight of 20 g/m² after carding to operate the roller card. The minimum web carding speed causing the web breakage once/hour on the card outlet side is defined as the high-speed carding performance.

Examples 1 to 11 and Comparative Examples 1 to 5

High-density polyethylene (HDPE) chips melted at 265° C. were used as a sheath component (heat bonding component) and polyethylene terephthalate (PET) having an intrinsic viscosity of 0.64 with orthochlorophenol solvent and melted at 290° C. was used as a core component (fiber-forming component). Both were fed to a core-sheath type conjugate spinneret having a hole diameter of 0.4 mm φ and 1,032 holes, discharged at a discharge temperature of the molten polymers of 250° C. and taken off at a speed of 1,100 m/min to provide a core-sheath type heat bonding conjugate fiber. At that time, the conjugate weight ratio of the core component to the sheath component was 50/50.

The resulting undrawn yarn was drawn at 70° C. at a draw ratio of 3.0 times, and treating agents containing compounds a to c, a POE-modified silicone (a molecular weight of 80,000 and a siloxane content of 40% by weight) and hexaglycerol monostearate described below in compositional ratios described in Table 1 as an aqueous emulsion at a concentration of 8% was applied to the fiber surfaces of the drawn yarn so as to provide the pickups as indicated in Table 1 according to the oil bath dipping method.

The above fibers were then passed through a stuffing crimper, provided with crimps at 13 peaks/25 mm and subsequently cut to afford staple fibers having a single fiber fineness of 2 denier and a fiber length of 50 mm. The hydrophilic property and high-speed carding performance of the resulting staple fibers were evaluated to show the obtained results in Table 1.

The Symbols in Table 1 Indicate the Following Compounds:

Compound a: a polyether polyester block copolymer comprising a polyether block composed of 100 moles of oxyethylene units randomly copolymerized with 30 moles of oxypropylene units and a polyester block composed of 50 moles of oxycaproyl units and the number of moles of the oxyalkylene units in said polyether block is 2.6 times that of the oxycaproyl units in said polyester block, Compound b: a higher alkyl ether having 25 carbon atoms of polyethylene glycol having a degree of polymerization of 50 and Compound c: potassium dodecenylsuccinate.

Examples 12 and 13

The same procedures as those in Example 1 were carried out, except that nylon-6 (Ny6) or polypropylene (PP) was used as the core component of the core-sheath type conjugate fiber in place of the PET. Table 1 shows the obtained results.

Example 14

The same procedures as those in Example 1 were carried out, except that a fiber comprising 100% of the HDPE was used in place of the core-sheath type conjugate fiber. Table 1 shows the obtained results.

Possibility of Industrial Utilization

The hydrophilic fiber of the present invention hardly causes the deterioration of hydrophilic performances even when exposed to conditions of high temperatures and high humidities for a long period and widely used for the whole products stored or used in the environments and requiring the hydrophilic property. Furthermore, the hydrophilic fiber of the present invention to which a treating agent containing the above metal alkenylsuccinate is applied has excellent high-speed carding performance of 140 m/min or above and a high value of industrial utilization due to its ability to remarkably improve the productivity when producing non-woven fabrics, spun yarns or the like.

TABLE 1

| | | | Composition of treating Agent | | | | | | Hydrophilic property of fiber | | |
|---|---|---|---|---|---|---|---|---|---|---|---|
| | | (1) | (2) | (3) | (4) | (5) | (6) | (7) | (8) | (9) | (10) | (11) |
| Example 1 | HDPE/PET | 0.35 | 15.0 | 30.0 | 20.0 | 0 | 35.0 | 8 | 4 | 200 | 170 |
| Example 2 | HDPE/PET | 0.20 | 15.0 | 30.0 | 20.0 | 0 | 35.0 | 10 | 5 | 200 | 162 |
| Example 3 | HDPE/PET | 1.00 | 15.0 | 30.0 | 20.0 | 0 | 35.0 | 7 | 3 | 233 | 170 |
| Example 4 | HDPE/PET | 0.35 | 5.0 | 30.0 | 20.0 | 0 | 45.0 | 10 | 6 | 167 | 160 |
| Example 5 | HDPE/PET | 0.35 | 50.0 | 30.0 | 20.0 | 0 | 0 | 3 | 1 | 300 | 160 |
| Example 6 | HDPE/PET | 0.35 | 15.0 | 15.0 | 20.0 | 0 | 50.0 | 10 | 8 | 125 | 155 |
| Example 7 | HDPE/PET | 0.35 | 15.0 | 65.0 | 20.0 | 0 | 0 | 5 | 4 | 125 | 160 |
| Example 8 | HDPE/PET | 0.35 | 15.0 | 30.0 | 5.0 | 0 | 50.0 | 5 | 5 | 100 | 140 |
| Example 9 | HDPE/PET | 0.35 | 30.0 | 30.0 | 40.0 | 0 | 0 | 10 | 5 | 200 | 145 |
| Example 10 | HDPE/PET | 0.35 | 0 | 30.0 | 20.0 | 0 | 50.0 | 10 | 9 | 111 | 150 |
| Example 11 | HDPE/PET | 0.35 | 15.0 | 0 | 20.0 | 0 | 65.0 | 13 | 12 | 108 | 145 |
| Comp. Example 1 | HDPE/PET | 0.35 | 15.0 | 30.0 | 0 | 0 | 55.0 | 10 | 13 | 77 | 90 |
| Comp. Example 2 | HDPE/PET | 0.35 | 0 | 0 | 0 | 100 | 0 | 14 | >60 | <23 | 80 |
| Comp. Example 3 | HDPE/PET | 0.35 | 0 | 0 | 0 | 0 | 100 | 3 | >60 | <5 | 90 |
| Comp. Example 4 | HDPE/PET | 0.35 | 0 | 50.0 | 0 | 50.0 | 0 | 14 | >60 | <23 | 80 |
| Comp. Example 5 | HDEP/PET | 0.35 | 0 | 0 | 0 | 30.0 | 70.0 | 3 | >60 | <5 | 90 |

TABLE 1-continued

|  | (1) | (2) | Composition of treating Agent | | | | | Hydrophilic property of fiber | | | |
|---|---|---|---|---|---|---|---|---|---|---|---|
|  |  |  | (3) | (4) | (5) | (6) | (7) | (8) | (9) | (10) | (11) |
| Example 12 | HDPE/PP | 0.35 | 15.0 | 30.0 | 20.0 | 0 | 35.0 | 7 | 3 | 233 | 150 |
| Example 13 | HDPE/Ny6 | 0.35 | 15.0 | 30.0 | 20.0 | 0 | 35.0 | 8 | 3 | 267 | 145 |
| Example 14 | HDPE/(100) | 0.35 | 15.0 | 30.0 | 20.0 | 0 | 35.0 | 8 | 3 | 267 | 155 |

(1) means 'Fiber composition (sheath component/core component)'.
(2) means 'Pickup of treating agent (wt. %)'.
(3) means 'Polyether polyester copolymer compound a (wt. %)'.
(4) means 'Polyoxyalkylene alkylether compound b (wt. %)'.
(5) means 'Metal alkenylsuccinate compound c (wt. %)'.
(6) means 'POE modified silicone (wt. %)'.
(7) means 'Hexaglycerol monostearate (wt. %)'.
(8) means 'Hydrophilic property before treatment with lapse of time (s)'.
(9) means 'Hydrophilic property after treatment at 40° C. × 80% with lapse of time (s)'.
(10) means 'Retention of hydrophilic property (%)'.
(11) means 'High-speed carding performance (m/min)'.
Comp. Example means 'Comparative Example'.

What is claimed is:

1. A hydrophilic fiber which is a fiber characterized in that the ratio of the perimeter occupied by a polyolefin to the whole perimeter of the fiber cross section is 30% or above and the hydrophilic property of the fiber is 30 seconds or below and the retention of the hydrophilic property of the fiber with the lapse of time is 90% or above, which properties are respectively defined as follows:

Hydrophilic Property of Fiber:

The interior of a pipe made of polymethyl methacrylate and having an inside diameter of 25 mm, an outside diameter of 30 mm and a pipe length of 25 mm is stuffed with 5.0 grams of fibers so as not to protrude the fibers. Said pipe is floated on 1,000 cc of softened water at 30° C. in a container having a caliber of 105 mm φ and filled with the water, allowed to stand and once sunk to the bottom. The fibers are then taken out of the interior of the pipe and air-dried at normal temperature. The operations are repeated four times, and the number of seconds required for the pipe from floating on the water to sinking to the bottom of the container is subsequently measured in the fifth operation to provide the hydrophilic property of the fiber.

Retention of Hydrophilic Property of Fiber with Lapse of Time:

When the hydrophilic property of the fiber before the treatment with lapse of time (at a temperature of 40° C. and a relative humidity of 80% for 30 days) measured according to the above method is $a_1$ and the hydrophilic property of the fiber after the treatment with lapse of time is $b_1$, the reciprocal (indicated by %) of $b_1/a_1$ is defined as the retention of hydrophilic property of the fiber with lapse of time.

2. A hydrophilic fiber which is a fiber characterized in that the ratio of the perimeter occupied by a polyolefin to the whole perimeter of the fiber cross section is 30% or above and a treating agent containing the component (A) and/or the component (B) described below in an amount of 15 to 95% by weight based on the active components of the treating agent and the component (C) described below in an amount of 5 to 40% by weight based on the active components of the treating agent in an amount of 0.05 to 5% by weight based on the weight of said fiber is applied to the surface of said fiber;

(A) A polyether polyester block copolymer comprising a polyether block composed of polyoxyalkylene units and polyester block composed of polyoxycaproyl units, (B) a higher alkyl ether of a polyoxyalkylene glycol having polyoxyethylene units and (C) a metal alenylsuccinate.

3. The hydrophilic fiber as set forth in claim 1 or 2, wherein the fiber is a conjugate fiber comprising the polyolefin and a polyester.

* * * * *